United States Patent
De Lange et al.

(10) Patent No.: US 9,150,562 B2
(45) Date of Patent: *Oct. 6, 2015

(54) PROCESS FOR THE PREPARATION OF DIOL SULFONES

(75) Inventors: Ben De Lange, Echt (NL); Peter Hans Riebel, Echt (NL); Michael Wolberg, Echt (NL); Dennis Heemskerk, Echt (NL); Daniel Mink, Echt (NL)

(73) Assignee: DSM SINOCHEM PHARMACEUTICALS NETHERLANDS B.V., Delft (NL)

( * ) Notice: Subject to any disclaimer, the term of this patent is extended or adjusted under 35 U.S.C. 154(b) by 27 days.

This patent is subject to a terminal disclaimer.

(21) Appl. No.: 13/980,154

(22) PCT Filed: Jan. 13, 2012

(86) PCT No.: PCT/EP2012/050468
§ 371 (c)(1),
(2), (4) Date: Jul. 17, 2013

(87) PCT Pub. No.: WO2012/098048
PCT Pub. Date: Jul. 26, 2012

(65) Prior Publication Data
US 2013/0303779 A1   Nov. 14, 2013

(30) Foreign Application Priority Data

Jan. 18, 2011 (EP) ..................................... 11151280

(51) Int. Cl.
| | | |
|---|---|---|
| C07D 405/12 | (2006.01) | |
| C07D 417/12 | (2006.01) | |
| C07D 413/12 | (2006.01) | |
| C07D 419/12 | (2006.01) | |

(52) U.S. Cl.
CPC ............ C07D 417/12 (2013.01); C07D 405/12 (2013.01); C07D 413/12 (2013.01); C07D 419/12 (2013.01)

(58) Field of Classification Search
CPC .................................................... C07D 405/12
See application file for complete search history.

(56) References Cited

FOREIGN PATENT DOCUMENTS

| EP | 0 414 206 A2 | 2/1991 |
|---|---|---|
| WO | 01/96311 A2 | 12/2001 |
| WO | WO 01/96311 | 12/2001 |
| WO | 02/098854 | 12/2002 |
| WO | WO 02/098854 | 12/2002 |
| WO | 2010/086438 | 8/2010 |
| WO | 2010/140765 | 12/2010 |

OTHER PUBLICATIONS

International Search Report for PCT/EP2012/050468 mailed Mar. 27, 2012.
J. Muñoz-Muriedas et al., "Hydrophobic Molecular Similarity from MST Fractional Contributions to the Octanol/Water Partition Coefficient", Journal of Computer-Aided Molecular Design, vol. 19, No. 6, Jun. 1, 2005, pp. 401-419.
N. Harris et al., "Acyl-COA: Cholesterol O-Acyl Transferase (ACAT) Inhibitors. 1. 1-(Alkylthio)-4,5-Diphenyl-1H-Imidazoles as Potent Inhibitors of Cat", Journal of Medicinal Chemistry, vol. 35, Jan. 1, 1992, pp. 4384-4392.
D.R. Sliskovic et al., "Inhibitors of Cholesterol Biosynthesis.4. trans-6-[2-(Substituted-quinolinyl) ethenyl/ethyl] tetrahydro-4-hydroxy-2H-pyran-2-ones, a Novel Series of HMG-CoA Reductase Inhibitors'", Journal of Medicinal Chemistry, 1991, vol. 34, No. 1, pp. 367-373.
Ueda et al, "Synthesis and Pharmacological Properties of N-[3-{-(1-Piperidinylmethyl)phenoxy}propyl]-2-(2-hydroxyethylthio)acetamide and Related Compounds as Antiulcer Agents. I," Chem. Pharm. Bull., vol. 38, No. pp. 3035-3041, 1990.
Sliskovic et al, Inhibitors of Chloresterol Biosynthesis, J.Med.Chem. 1991, 34, 367-373.
Harris et al; Acyl-CoA:cholesterol O-Acyl Transferase (ACAT) Inhibitors, J.Med.Chem. 1992, 35, 4384-4392.
Muñoz-Muriedas et al, Hydrophobic molecular similarity from MST fractional contributions to the octanol/water partition coefficient, J.Computer-Aided Molecular Design (2005) 19: 401-419.

*Primary Examiner* — Andrew D Kosar
*Assistant Examiner* — John S Kenyon
(74) *Attorney, Agent, or Firm* — Nixon & Vanderhye P.C.

(57) ABSTRACT

The present invention relates to a process for the preparation of a diol sulfone derivative comprising reaction of a halomethyl substrate with a thio-aryl compound to obtain a thio-ether compound, and oxidizing the thio-ether compound to the corresponding sulfone. In case of a chiral halomethyl substrate, the resulting chiral diol sulfone derivative is suitable as a building block for statin type compounds.

11 Claims, No Drawings

PROCESS FOR THE PREPARATION OF DIOL SULFONES

This application is the U.S. national phase of International Application No. PCT/EP2012/050468 filed 13 Jan. 2012 which designated the U.S. and claims priority to EP 11151280.2 filed 18 Jan. 2011, the entire contents of each of which are hereby incorporated by reference.

FIELD OF THE INVENTION

The present invention relates to a process for the preparation of a diol sulfone derivative comprising reaction of a halomethyl substrate with a thio-aryl compound to obtain a thio-ether compound, and oxidizing the thio-ether compound to the corresponding sulfone. In case of a chiral halomethyl substrate, the resulting chiral diol sulfone derivative is suitable as a building block for statin type compounds.

BACKGROUND OF THE INVENTION

In a first aspect, the invention relates to a process for preparing chiral diol sulfones, which are advanced intermediates used in preparing statins, a class of compounds useful as HMG CoA reductase inhibitors.

A method for preparing chiral diol sulfones is described in WO 2002/098854 and WO 2001/096311 wherein a sulfone is prepared from an alcohol, more in particular tert-butyl 2-(4R,6S)-6-(hydroxymethyl)-2,2-dimethyl-1,3-dioxan-4-yl)acetate known as "Kaneka alcohol". The preparation of such an alcohol is described in EP 1024139.

The synthesis of the sulfone in the prior art has a disadvantage, in that trifluoromethanesulfonic anhydride or another sulfonic acid derived activating agent is used to activate the alcohol function to an extent that a nucleophilic attack with a thiol is possible. Trifluoromethanesulfonic anhydride is an extremely hazardous and expensive component, which causes costly work-up procedures due to environmentally problematic waste streams. In WO 2010/140765 this problem has been addressed by direct reaction of a halomethyl derivative of a very specific and highly sterically hindered 2-methyl-1-phenylpropan-2-yl ester. Although this represents a first example of a direct nucleophilic attack by a thiol compound on a halide, the bulkiness of the ester group inherently also prevents the side reaction of unwanted substitution of the ester moiety leading to unwanted thio-ester.

It is an object of the present invention to provide a process, in which not only the use of an activating agent like trifluoromethanesulfonic anhydride is omitted but which is also applicable to esters of sterically unhindered and/or small alcohols such as butyl esters, ethyl esters, methyl esters and propyl esters.

DETAILED DESCRIPTION OF THE INVENTION

In the process of the invention, a compound of formula (1) or the corresponding lactone form (1') can be used as starting material

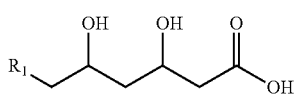

(1)

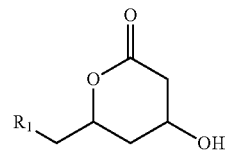

(1')

wherein $R_1$ stands for halogen, like bromine or chlorine, preferably chlorine.

Prior to use in the process of the invention the hydroxyl groups and the carboxyl group of the above compounds may be protected as ketal and ester as outlined in general formula (1a) or as lactone and ether as outlined in general formula (1b)

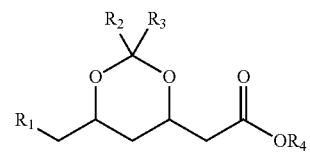

(1a)

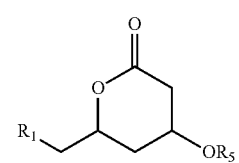

(1b)

wherein $R_2$ and $R_3$ each independently stand for an alkyl with for instance 1 to 12 C-atoms, preferably 1 to 6 C-atoms, an alkenyl with for instance 1 to 12 C-atoms, preferably 1 to 6 C-atoms, a cycloalkyl with for instance 3 to 7 C-atoms, a cycloalkenyl with for instance 3 to 7 C-atoms, an aryl with for instance 6 to 10 C-atoms or an aralkyl with for instance 7 to 12 C-atoms, each of $R_2$ and $R_3$ may be substituted and wherein $R_2$ and $R_3$ may form a ring together with the C-atom to which they are bound, use being made of a suitable acetal forming agent, in the presence of an acid catalyst, for example as described in WO 2002/06266. The groups $R_2$ and $R_3$ are for example halogens or hydrocarbon groups with for instance 1 to 10 C-atoms, optionally containing one or more heteroatoms, for instance Si, N, P, O, S, F, Cl, Br or I. In practice, $R_2$=$R_3$ is methyl is most preferred. In the compound of general formula (1a) $R_4$ is an alkyl or alkenyl group with one, two, three or four carbon atoms. Such relatively small substituents are generally known as being sterically unhindered or at least not very bulky. Suitable examples are allyl, iso-butenyl, n-butyl, sec-butyl, tert-butyl, ethyl, methyl, n-propyl, iso-propyl and vinyl. Preferably $R_4$ is a group that is easily introduced, small and easily removed under acidic conditions such as ethyl, methyl or iso-propyl. In the compound of general formula (1b) $R_5$ is hydrogen or an alcohol protecting group. Such a group can be any alcohol protecting group known to the skilled person such as described in, for example "Protective Groups in Organic Synthesis" (T. W. Greene, 1981, Wiley-Interscience Publication, ISBN 0-471-05764-9). These protecting groups are for example esters or ethers. These protection groups are preferred because in the final stage of conversion of these building blocks to statins, these generally acid labile or basic labile (in the case of esters) protection groups have the advantage to be removed either simultaneously with the opening of the lactone ring or by a pH shift. Hence, suitable groups $R_5$ are allyl, benzyloxymethyl, tert-butoxymethyl, tert-butyl, methoxymethyl, 1-ethoxyethyl, methoxyethoxymethyl, 4-methoxytetrahydropyranyl, methylthiomethyl, 1-(iso-propoxy)ethyl, tetrahydrofuranyl, tetrahydropyranyl, 2-methoxypropanyl, 1-propenyl, acetate, chloroacetate or benzoate. The compounds of general formula (1b) have the additional advantage that the internal ester linkage between the carboxylic acid group and one of the hydroxyl groups in (1) forming the lactone group in (1b) function as protection without any added atoms that are to be removed later on in the process. Consequently no auxiliary chemicals are required for protection, no waste is generated during deprotection and there is no need for complex and/or energy-consuming recycling approaches. The compounds of formula (1) and (1'), and hence the compounds of formula (1a) and (1b) can be either enantiomerically pure or enriched in one of the enantiomers or racemic.

The compounds of formula (1a) or (1b) are reacted with a thiol compound of general formula $R_6$—S—X (2) to give a compound of general formula (3a) or (3b), respectively with $R_2$, $R_3$, $R_4$ and $R_5$ as defined above.

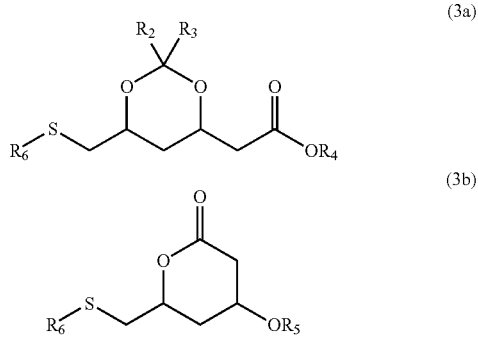

In the compound of general formula (2), X represents a proton or another cation like, for example, an alkali metal ion, like sodium or potassium or lithium cation, or an ammonium ion, like tetraalkylammonium, or a phosphonium ion, like tetraalkylphosphonium. $R_6$ is an aryl group that for instance is suitable for a one-pot or modified Julia-Kocienski olefination. The Julia-Kocienski olefination is a reaction in which a sulfone is reacted with an aldehyde to form an olefinic (double) bond. The original Julia olefination requires two steps. In the modified reaction (Julia-Kocienski olefination), the intermediate obtained in the reaction with an aldehyde undergoes spontaneous elimination to give the olefin.

Preferably, the aryl group is a residue sufficiently π-electron deficient to be suitable for the modified (or one-pot) Julia-Kocienski olefination. In particular, it is preferred, that the aryl group is capable to promote a so-called Smiles rearrangement. Preferably, the thiol-aryl compound contains as an aryl group an aromatic moiety having a hetero atom, more preferably nitrogen. More in particular, the aromatic residue contains an electrophilic imine-like moiety within the heterocycle. Suitable aryl groups are e.g. described in P. R. Blakemore, J. Chem. Soc., Perkin Trans. 1, 2002, 2563. Preferred aryl groups include tetrazole, substituted phenyl and benzimidazole type compounds. Specific examples of preferred aryl groups include, pyridine-2-yl, pyrimidin-2-yl, benzothiazol-2-yl, 1-methyl-1H-tetrazol-5-yl, 1-phenyl-1H-tetrazol-5-yl, 1-tert-butyl-1-H-tetrazol-5-yl, 3,5-bis(trifluoromethyl)phenyl-1-yl, 1-methylimidazol-2-yl, benzimidazol-2-yl, 4-methyl-1,2,4-triazol-3-yl and iso-quinolin-1-yl. Most preferred aryl groups are 1-methyl-1H-tetrazol-5-yl, 1-phenyl-1H-tetrazol-5-yl, 1-tert-butyl-1-H-tetrazol-5-yl, benzothiazol-2-yl, and 3,5-bis(trifluoromethyl)phenyl-1-yl.

The reaction will take place under suitable conditions wherein it is generally important to preclude harsh conditions (like temperatures above 130° C. or exceedingly long reaction times or application of strongly basic or acidic conditions) in order to preclude degradation of the starting compound or the thiol obtained. Suitable reaction conditions are temperatures about 50° C. or higher, preferably about 80° C. or higher, and more in particular about 100° C. or higher. Generally, the temperature will be about 150° C. or lower, preferably about 140° C. or lower, and more in particular about 130° C. or lower. In case a temperature at the higher end-range is chosen, care should be taken to choose the time period such, that limited degradation occurs. Limited degradation is less than 10% of the starting halomethyl compound of general formula (1a) or (1b), preferably less than 5%, more in particular less than about 3%. Generally, a reaction time of less than about 20 h, preferably less than about 10 h should be possible in case the reaction conditions are chosen properly. However, the time period is not critical, and may be up to 30 h or longer. Generally, the reaction takes longer than about 1 h, but this is strongly dependant on the reaction conditions, reaction engineering aspects (like reactor design or application of rate-accelerating means like application of ultrasound or microwave irradiation) and amounts of reagents used, and this is not critical.

The reaction to obtain the thio-ether can be performed in a solvent or without the presence of a solvent. In case a solvent is used, the concentration of halomethyl starting compound of general formula (1a) or (1b) is generally about 10 wt % or higher, preferably about 30 wt % or higher, more in particular about 40 wt % or higher. Preferably, the reaction is carried out with a relatively high concentration of halomethyl starting compound of general formula (1a) or (1b) of 70 to 99 wt %.

Suitable solvents are dimethylsulfoxide (DMSO), N-methylpyrrolidone (NMP), dimethylformamide (DMF), sulfolane, acetonitrile, glymes (alkyl-capped or uncapped mono-, oligo-, or poly-ethylene glycol ethers of varying chain length) or other polar non-protic solvents or alcohols like methanol, ethanol, 2-propanol, or halogenated hydrocarbons like dichloromethane, chloroform, 1,2-dichloroethane, optionally in combination with non-polar solvents like toluene or methyl tert-butyl ether (MTBE). It is also possible to use biphasic solvent systems consisting of an aqueous phase and an organic phase in the presence of a phase-transfer catalyst, like quaternary ammonium salt or quarterly phosphonium salt (like tetraalkylammonium halide, e.g. tetrabutylammonium bromide) or crown ether (like 18-crown-6). These phase transfer-catalysts are also very suitable for use in mono-phasic solvent systems. Another class of suitable solvents comprises ionic liquids like, for example, 1,3-dialkyl imidazolium salts or N-alkyl pyridinium salts of acids like hexafluorophosphoric acid or tetrafluoroboric acid or trifluoromethane sulfonic acid, or with $(CF_3SO_2)_2N^-$ as anionic counterpart.

The amounts of reagents can be chosen from a wide range. It is preferred to use a rate-enhancing excess of thiol compound, as the excess thiol that remains after reaction with the halomethyl derivative can be easily removed by washing with water at high pH. The molar amount of thiol to halogen compound generally is about 0.5 to 1 or higher, preferably 1 to 1 or higher, more preferably 1.1 to 1 or higher. Generally, the amount of thiol to halogen compound will be 3 to 1 or lower, preferably 2 to 1 or lower, most preferably 1.5 to 1 or lower. Preferably excess thiol is recovered for re-use which is easily achieved with the thiols of the present invention.

The compound of formula (3a) or (3b) can be isolated from the reaction mixture, or the mixture can be used as such in a subsequent oxidation reaction. Preferably, the reaction mixture is treated so as to remove excess thiol compound or excess halogen compound as the case may be. Any excess thiol compound can be easily removed by extraction with water at pH higher than 7, preferably higher than 8, more preferably of about 9 or higher. Suitable extraction agents are for example saturated caustic soda solution, saturated bicarbonate solution, or diluted sodium hydroxide solution. After extraction, the thio-ether compound of general formula (3a) or (3b) can be isolated by removal of the solvent by distillation, or by crystallization or precipitation, e.g. by addition of (or solvent switch to) an anti-solvent like hexane, heptane, iso-octane, or water. It is however not necessary to remove the solvent, as the oxidation can be performed in the same solvent. It is however preferred, to remove water from the reaction mixture, in case water interferes with the oxidation reaction. Hence, in a preferred embodiment of the invention, the oxidation is carried out without purification of the thio-ether compound of general formula (3a) or (3b), more preferably in the same solvent as was used in the etherification reaction.

According to the process of the invention, a halogen derivative can be used as starting compound. This is advantageous because the Kaneka alcohol generally is prepared from such a halogen derivative. Therefore, the present invention provides a process, in which additional steps in the prior art are made obsolete if the chiral diol sulfone is to be used in a Julia-Kocienski olefination.

It was unexpected, that the thio-ether compound of general formula (3a) or (3b) could be prepared in this way, because a nucleophilic attack on a halomethyl group (in particular a chloromethyl group) in the presence of an alkoxy substituent in beta-position to the halogen is known to be extremely difficult [cf. a) Methoden der Organischen Chemie (Houben-Weyl), vol. V/4, 1960, p. 700; b) M. E. Jung et al, J. Org. Chem. 1998, 63, 347-355 and ref. 17 cited therein; c) D. G. Bourke et al., Aust. J. Chem. 1996, 49, 425-434]. This holds especially in cases where said alkoxy substituent is part of a cyclic ether moiety like the 1,3-dioxane moiety as exemplified in the compound of formula (1a). Drastic reaction conditions like a 20-fold excess of the nucleophile and/or reaction times of up to weeks are necessary to obtain a useful conversion [cf. a) WO 2003/004459 and references cited therein, b) W. E. Willy et al., Bull. Chem. Soc. Japan 1976, 49, 1989-1995 (see table 1, entry 11); c) S. D. Rychnovsky et al, J. Org. Chem. 1992, 57, 1559-1563; d) M. Kabeya et al., Tetrahedron 1997, 53, 9777-9788]. On the other hand, harsh conditions will lead to decomposition and/or to racemization (or epimerization, respectively) of the diol function in the case of compounds like shown in formula (1). Therefore, it was unexpected, that this reaction could be carried out under mild conditions that allowed more than 80% yield, and even more than 90% yield in combination with less that 5% degradation of the starting compound, or even less than 3% degradation.

Where nucleophilic attack on a halomethyl group appears successful in WO 2010/140765, this could not be anticipated in the presence instance where the substrate molecules of general formula (1a) and (1b) all have small and relatively unhindered carboxylic acid protecting groups such as methyl or iso-propyl. It is well-known that such small and unhindered moieties easily undergo degradation. Moreover, especially in the presence of thiols such small moieties can form thioesters. These unwanted side reactions are not to be predicted for highly sterically hindered esters such as the 2-methyl-1-phenylpropan-2-yl ester presented in WO 2010/140765.

The thio-ether compound of formula (3a) or (3b) is oxidized as known in the art, i.e. by oxidation with hydrogen peroxide or other oxidants like peracids (e.g. 3-chloro-peroxybenzoic acid, peroxyacetic acid, monoperoxyphthalic acid), bleach, tert-BuOCl, perborates, N-oxides, permanganate, chromate, chlorate, bromate, perchlorate, periodate, tert-butyl hydroperoxide, oxone, peroxodisulfates and air/oxygen. If necessary, the oxidation can be carried out in the presence of an appropriate catalyst, such as salts or oxides of the metals V, Ce, Mn, Ni, Fe, Cu, Os, Mo, W, Re, or Ru or organic catalysts like iso-butyraldehyde in the case of air/oxygen or tetramethylpiperidine N-oxide (TEMPO) in the case of bleach. The resulting sulfones are of general formula (4a) and (4b), respectively, with $R_2$, $R_3$, $R_4$, $R_5$ and $R_6$ as defined above.

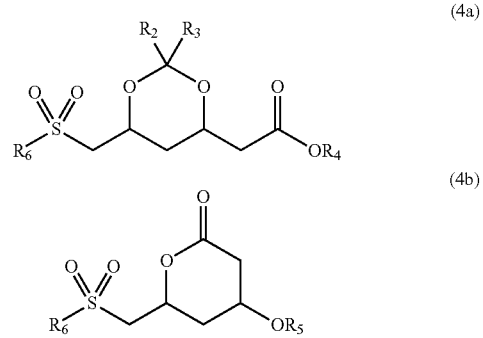

The oxidation generally is performed in a solvent, such as dichloromethane, chloroform, 1,2-dichloroethane, methanol, ethanol, 2-propanol, acetonitrile, acetic acid, toluene, water, NMP, DMSO, DMF, tetrahydrofuran (THF), or MTBE. It is also possible to use biphasic solvent systems consisting of an aqueous phase and an organic phase in the presence of a phase-transfer catalyst, like quaternary ammonium salt or quarterly phosphonium salt (like tetraalkylammonium halide, e.g. tetrabutylammonium bromide) or crown ether (like 18-crown-6). Another class of suitable solvents comprises ionic liquids like, for example, 1,3-dialkyl imidazolium salts or N-alkyl pyridinium salts of acids like hexafluorophosphoric acid or tetrafluoroboric acid or trifluoromethane sulfonic acid, or with $(CF_3SO_2)_2N^-$ as anionic counterpart. Generally, a reaction temperature of about −20° C. or higher is effective.

Preferably, a temperature of 0° C. or higher is applied, more preferably close to ambient temperature (18-25° C. i.e. around 20° C.). A temperature of about 150° C. or lower generally is effective to bring about the oxidation. Generally, the reaction temperature will be about 100° C. or lower, more preferably about 60° C. or lower, most preferably about 40° C. or lower. The molar amount of oxidant to thio-ether generally is about 1 to 1 or higher, preferably about 2 to 1 or higher, more preferably about 3 to 1 or higher. Generally, the amount of terminal oxidant to thio-ether will be about 20 to 1 or lower, preferably about 10 to 1 or lower, most preferably about 5 to 1 or lower.

The sulfone of general formula (4a) or (4b) can be isolated by aqueous extraction of excess oxidant/catalyst and subsequent removal of the solvent by evaporation. If water-miscible solvents like alcohols or aprotic polar solvents are applied as reaction medium, the reaction mixture can be partitioned between an aqueous and an organic phase prior to this operation, in order to extract the solvent to the aqueous phase. If ionic liquids are applied as reaction medium, the sulfone can be isolated by extraction with an organic solvent immiscible with the ionic liquid, followed by evaporation of the solvent. Alternatively, the sulfone can be isolated from the reaction mixture by precipitation or crystallization, e.g. by addition of (or solvent switch to) an anti-solvent like hexane, heptane, iso-octane, or water. If desired, purification of the sulfone can be performed by chromatography or, preferably, by re-crystallization from (or trituration with) a suitable solvent, like 2-propanol or another solvent, depending on the aryl group used with the thiol compound of formula (2) and the residues $R_2$, $R_3$, $R_4$ and $R_5$ used with the initial halomethyl compounds of formula (1a) or (1b).

In one embodiment, the sulfone of general formula (4a) or (4b) is treated with an aldehyde $R_7$—CH═O, in which $R_7$ is chosen so as to obtain suitable precursors to useful statin-type compounds including pitavastatin, rosuvastatin, fluvastatin, and cerivastatin, or in which $R_7$ is a suitable precursor to these moieties (cf. WO 2002/098854 and WO 2001/096311). Preferred examples of aldehyde $R_7$—CH═O are 4-(4-fluorophenyl)-2,6-diisopropyl-5-(methoxymethyl)nicotinaldehyde, 3-(4-fluorophenyl)-1-isopropyl-1H-indole-2-carbaldehyde, 2-cyclopropyl-4-(4-fluorophenyl)quinoline-3-carbaldehyde and N-(4-(4-fluorophenyl)-5-formyl-6-isopropylpyrimidin-2-yl)-N-methylmethanesulfonamide as these aldehydes are the precursors for cerivastatin, fluvastatin, pitavastatin and rosuvastatin, respectively.

The so-called Julia-Kocienski olefination between compounds (4a) or (4b) and aldehyde $R_7$—CH═O preferably is carried out in the presence of a base, examples of which are lithium hydride, potassium hydride, sodium hydride, lithium hexamethyldisilazane (LiHMDS), sodium hexamethyldisilazane (NaHMDS), potassium hexamethyldisilazane (KHMDS), solid potassium hydroxide, solid sodium hydroxide, metal alkoxides, such as sodium methoxide, lithium methoxide and potassium methoxide, lithium tert-butoxide, potassium tert-butoxide, sodium tert-butoxide, lithium bis-trimethylsilylamide (LiN(TMS)$_2$), sodium bis-trimethylsilylamide (NaN(TMS)$_2$), potassium bis-trimethylsilylamide (KN(TMS)$_2$), sodium amide, P4-tBu and 1,8-diazabicyclo[5.4.0]undec-7-ene (DBU) and the like. Whereas the E/Z-ratio in the final product depends on various parameters, such as type of base, thio-substituent ($R_6$) and solvents, as for instance outlined in P. R. Blakemore, W. J. Cole, P. J. Kocienski and A. Morley, Synlett 1998, 26-28, this ratio normally varies between 40:60 and 80:20 in customary solvents such as diethyl ether, dimethoxyethane, tetrahydrofuran and toluene.

Surprisingly it was found that in the condensation reaction of the present invention, i.e. starting from compounds of general formula (4a) and (4b) and aldehydes $R_7$—CH═O there was a marked difference between lithium-comprising bases and sodium-comprising bases where the latter strongly favored extremely high E/Z-ratio's. For example, when using LiHMDS an E/Z-ratio of 70:30 was achieved whereas the use of NaHDMS led to an E/Z-ratio of >99:1. This is advantageous as the E-configuration is the required configuration in cerivastatin, fluvastatin, pitavastatin and rosuvastatin. Hence, the use of a sodium-comprising base precludes laborious removal and/or recycling of undesired Z-isomer.

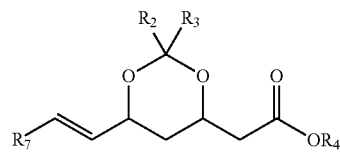

(5a)

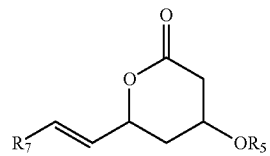

(5b)

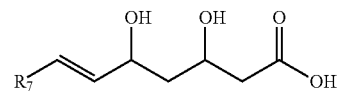

(6)

Following the Julia-Kocienski olefination between compounds (4a) or (4b) and aldehyde $R_7$—CH═O the resulting products (5a) and (5b), respectively may be isolated and purified after which they are deprotected to give product (6). Alternatively deprotection may be carried out without isolation and/or purification of intermediate products (5a) and (5b). Deprotection is carried out according to procedures known to the skilled person, for instance by using acid such as hydrochloric acid as described in U.S. Pat. No. 6,844,437 or WO 2007/000121.

In a second aspect, the invention relates to novel compounds of general formula (3b) or (4b)

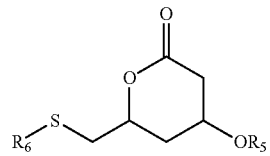

(3b)

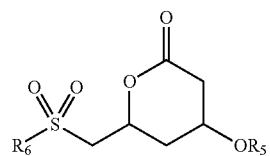

(4b)

wherein $R_5$ is hydrogen or an alcohol protecting group as defined above an $R_6$ is as defined above, in particular a group suitable for the Julia-Kocienski olefination as outlined in the first aspect of the invention. Particularly suitable in this respect are substituents $R_6$ of general formula $R_{6'}$, and $R_{6''}$

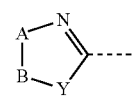

($R_{6'}$)

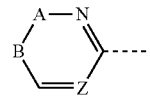

($R_{6''}$)

wherein A-B is C═C or N═N or wherein A-B is part of a aromatic five- or six-membered ring, wherein Y is sulfur or alkyl-substituted nitrogen, preferably tert-butyl-substituted nitrogen, ethyl-substituted nitrogen, methyl-substituted nitrogen or phenyl-substituted nitrogen and wherein Z is nitrogen or CH. Particularly suitable examples of $R_6$ are tetrazole and benzimidazole type compounds. Specific examples of preferred aryl groups include pyridine-2-yl, pyrimidin-2-yl, benzothiazol-2-yl, 1-methyl-1H-tetrazol-5-yl, 1-phenyl-1H-tetrazol-5-yl, 1-tert-butyl-1-H-tetrazol-5-yl, 1-methylimidazol-2-yl, benzimidazol-2-yl, 4-methyl-1,2,4-triazol-3-yl and iso-quinolin-1-yl. Most preferred aryl groups are 1-methyl-1H-tetrazol-5-yl, 1-phenyl-1H-tetrazol-5-yl, 1-tert-butyl-1-H-tetrazol-5-yl and benzothiazol-2-yl.

The compounds of the second aspect of the invention are well suited as easily accessible intermediates in the synthesis of statins such as cerivastatin, fluvastatin, pitavastatin and rosuvastatin and may be prepared according to the process of the first aspect of the invention.

EXAMPLES

Example 1

Preparation of 2-((4R,6S)-2,2-dimethyl-6-((1-phenyl-1H-tetrazol-5-ylthio)methyl)-1,3-dioxan-4-yl) acetic acid tert-butyl ester (B) from (4R,6S)-6-(chloromethyl)-2,2-dimethyl-1,3-dioxan-4-yl)acetic acid tert-butylester (A) and sodium-1-phenyl-1H-tetrazole-5-thiolate (SPTT)

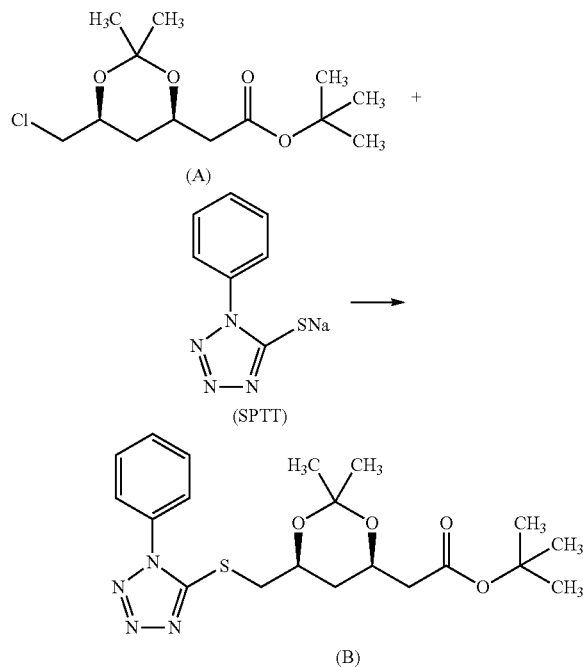

Example 1a

Reaction Conditions: 5.5 h at 80° C. And 5 h at 100° C.

A mixture of (4R,6S)-6-(chloromethyl)-2,2-dimethyl-1,3-dioxan-4-yl)acetic acid tert-butyl ester (compound A, 1.4 g, 5.0 mmol, >99% ee, obtained from DSM Pharma Chemicals), phenyl tetrazole sodium thiolate (SPTT, 1.5 g, 7.5 mmol) and NMP (6 mL) was heated under argon at 80° C. for 5.5 h with stirring and at 100° C. for another 5 h. The mixture was cooled to 20-25° C. and partitioned between 50 mL of MTBE and 25 mL of water. Phases were separated and the organic phase was washed successively with aqueous hydrochloric acid (1N), saturated aqueous $NaHCO_3$ and brine. Evaporation of the solvent in vacuo at 50° C. afforded 2-((4R,6S)-2,2-dimethyl-6-((1-phenyl-1H-tetrazol-5-ylthio)methyl)-1,3-dioxan-4-yl)acetic acid tert-butyl ester (thio ether B) as a dark orange syrup. This syrup was essentially pure except for the presence of a small residual amount of MTBE, as was judged from $^1$H- and $^{13}$C-NMR analysis. Yield 2.1 g (5.0 mmol, 99%). $^1$H-NMR (400 MHz, $CDCl_3$): δ=1.34 (s, 3H); 1.37-1.46 (m, 1H) superimposed on 1.42 (s, 3H) and 1.43 (s, 9H); 1.73-1.77 (m, dt-like, 1H); 2.31 (dd, J=15.2, 5.9 Hz, 1H); 2.42 (dd, J=15.2, 7.2 Hz, 1H); 3.38 (dd, J=13.4, 7.4 Hz, 1H); 3.61 (dd, J=13.4, 3.9 Hz, 1H); 4.22-4.30 (m, 2H); 7.52-7.60 (m, 5H). $^{13}$C-NMR (100 MHz, $CDCl_3$): δ=19.9 ($CH_3$); 28.3 ($C(CH_3)_3$); 30.0 ($CH_3$); 35.4, 38.9, 42.7 (C2, C4, C6); 66.1, 67.8 (C3, C5); 81.0 ($C(CH_3)_3$); 99.5 ($C(CH_3)_2$); 124.1, 130.0, 130.35 (Ar—$C_p$); 133.85 (Ar—$C_q$); 154.7 (tetrazole-$C_q$); 170.1 (C1).

Example 1b

Reaction Conditions: 14 h at 90-95° C., 2 h at 100° C. And 2 h at 115-120° C.

In a 50 mL round bottom flask equipped with a reflux condenser, gas inlet, and magnetic stirring bar, compound A (2.8 g, 10.0 mmol) was dissolved in NMP (12 mL). Then SPTT (2.5 g, 12.5 mmol) was added under an argon atmosphere. The reactants were mixed by magnetic stirring and the flask was immersed in an oil bath at 90-95° C. for 14 h. The temperature of the oil bath was increased to 105-110° C. for 2 h and to 115-120° C. for another 2 h. The mixture was cooled to 20-25° C. and partitioned between 100 mL of MTBE and 50 mL of water. Work-up as described in Example 1a yielded product B as dark orange syrup (4.2 g, 99%).

Example 1c

Reaction Conditions: 3 h at 120° C. And 1.5 h at 130° C.

In a 100 mL 3-necked round bottom flask equipped with a reflux condenser, gas inlet, and a mechanical stirrer, compound A (14.0 g, 50 mmol) was dissolved in NMP (50 mL) and SPTT (12.5 g, 62.5 mmol) was added under an argon atmosphere. The mixture was heated at 120° C. for 3 h with stirring and at 130° C. for another 1.5 h. The mixture was cooled to 20-25° C. and partitioned between 250 mL of MTBE and 250 mL of water. Phases were separated and the aqueous phase was extracted with another 100 mL of MTBE. The combined organic phases were washed successively with aqueous hydrochloric acid (1N, 50 mL), saturated aqueous $NaHCO_3$ (50 mL) and brine (50 mL). Evaporation of the solvent in vacuo at 50° C. afforded thio-ether B as orange-brown syrup. Yield 22.9 g (54.5 mmol, 109%, oil contains a small amount of MTBE).

Example 1d

DMSO as Solvent Instead of NMP

A mixture of compound A (1.4 g, 5.0 mmol, >99% ee), SPTT (1.25 g, 6.3 mmol) and DMSO (5 mL) was heated under argon at 120° C. for 2.5 h with stirring. The mixture was cooled to 20-25° C. and partitioned between 25 mL of ethyl acetate and 25 mL of water. Phases were separated, and the aqueous phase was extracted with another 10 mL of ethyl acetate. The combined organic phases were successively washed with saturated aqueous sodium bicarbonate solution (10 mL), and brine (10 mL). Drying over anhydrous magnesium sulfate followed by filtration and evaporation of the solvent in vacuo at 50° C. afforded thio-ether B as yellow-brown syrup. Yield 2.13 g (101%, oil contains a small amount of residual ethyl acetate).

Example 2

Preparation of 2-(4R,6S)-2,2-dimethyl-6-(1-phenyl-1H-tetrazol-5-ylsulfonyl)methyl)-1,3-dioxan-4-yl) acetic acid tert-butyl ester (C) from 2-(4R,6S)-2,2-dimethyl-6-(1-phenyl-1H-tetrazol-5-ylthio)methyl)-1,3-dioxan-4-yl)acetic acid tert-butyl ester (B)

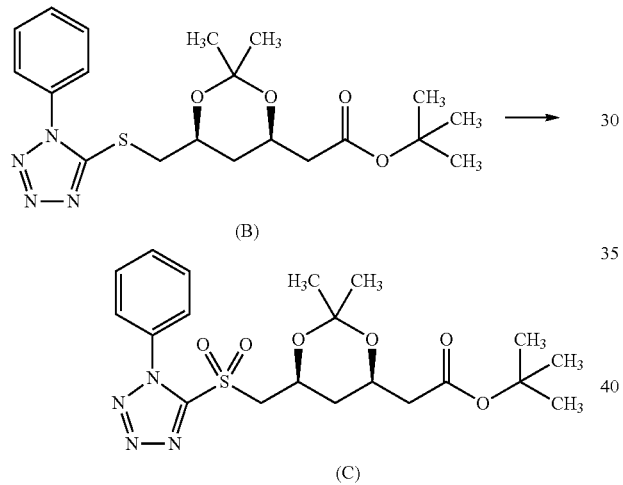

In a 3-necked round bottom flask equipped with a reflux condenser, gas inlet, and mechanical stirrer, 2-((4R,6S)-2,2-dimethyl-6-(((1-phenyl-1H-tetrazol-5-ylthio)methyl)-1,3-dioxan-4-yl)acetic acid tert-butyl ester (Compound B, 2.1 g, 5.0 mmol) as obtained in Example 1 was dissolved in $CH_2Cl_2$ (50 mL) and $NaHCO_3$ (1.5 g, 17.9 mmol) was added. The mixture was cooled to 2° C. in an ice-bath and meta-chloroperbenzoic acid (3.3 g, 13.3 mmol, 70% purity) was added. The ice-bath was removed and the mixture was stirred 16 h at 20-25° C. $CH_2Cl_2$ (20 mL) and saturated aqueous $NaHCO_3$ (40 mL) were added and the resulting phases were separated. The organic phase was washed with aqueous HCl (1 N) and saturated aqueous $NaHCO_3$, dried over $Na_2SO_4$ and evaporated in vacuo to dryness, leaving crude 2-((4R,6S)-2,2-dimethyl-6-(((1-phenyl-1H-tetrazol-5-ylsulfonyl)methyl)-1,3-dioxan-4-yl)acetic acid tert-butyl ester (Compound C) as a yellow highly viscous syrup that solidified after storage for some hours at 20-25° C. (2.3 g). The crude product was recrystallized from isopropanol and dried at 50° C. in vacuo to give compound C in 73% yield (1.65 g, 3.8 mmol), m.p. 128.5-129.5° C., $[alpha]^{23}_D=-14.3$ (c=2, ethyl acetate). Of the product thus obtained, a portion of 1.2 g was re-crystallized from isopropanol to give analytically pure product C in 92% recovery yield (1.1 g), m. p. 137.4-137.6° C., $[alpha]^{23}_D=-14.9$ (c=2, ethyl acetate). $^1$H-NMR (400 MHz, $CDCl_3$): δ=1.05 (s, 3H); 1.14-1.25 (m, 1H); 1.30 (s, 3H); 1.39 (s, 9H); 1.57-1.63 (m, dt-like, 1H); 2.25 (dd, J=15.3, 6.0 Hz, 1H); 2.35 (dd, J=15.3, 7.1 Hz, 1H); 3.38 (dd, J=15.0, 3.2 Hz, 1H); 3.43 (dd, J=15.0, 8.5 Hz, 1H); 4.21 ($m_c$, 1H); 4.50 ($m_c$, 1 H); 7.56-7.66 (m, 5H). $^{13}$C-NMR (100 MHz, $CDCl_3$): δ=19.2 ($CH_3$); 28.15 ($C(CH_3)_3$); 29.5 ($CH_3$); 34.8, 42.3 (C2, C4); 61.0 (C6); 64.6, 65.7 (C3, C5); 81.0 ($C(CH_3)_3$); 99.4 ($C(CH_3)_2$); 126.1, 129.8, 131.8 (Ar—$C_p$); 133.0 (Ar—$C_q$); 154.4 (tetrazole-$C_q$); 169.6 (C1). The spectroscopic data of compound C are in accordance with the data given in WO 2002/098854.

Example 3

Preparation of 2-(4R,6S)-6-((benzo[d]thiazole-2-ylthio)methyl)-2,2-dimethyl-1,3-dioxan-4-yl)acetic acid tert-butyl ester (D) from (4R,6S)-6-(chloromethyl)-2,2-dimethyl-1,3-dioxan-4-yl)acetic acid tert-butylester (A) and 2-mercapto-1H-benzothiazole (2-MBT)

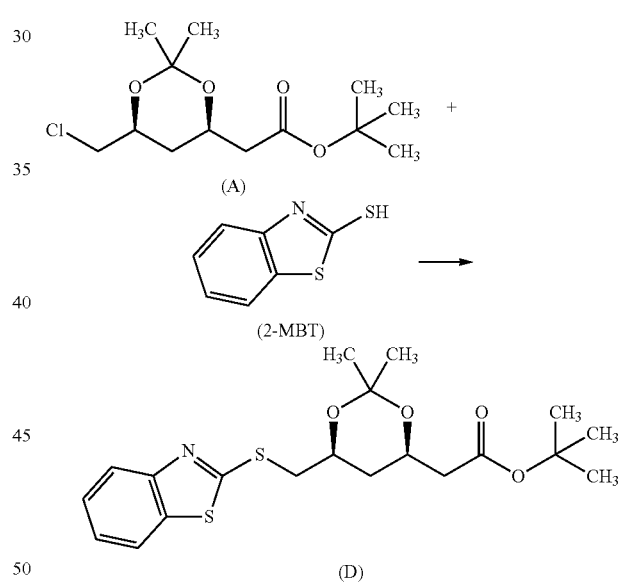

(4R,6S)-6-(chloromethyl)-2,2-dimethyl-1,3-dioxan-4-yl) acetic acid tert-butyl ester (A, 5.56 g, 20.0 mmol) was dissolved in 50 mL of NMP. Then $NaHCO_3$ (3.36 g, 40.0 mmol) and tetrabutylammonium bromide (0.35 g) were added. To the stirred mixture was added 2-mercapto-1H-benzothiazole (2-MBT, 3.67 g, 22.0 mmol). The mixture was heated to 130° C. and kept at this temperature for 6 h. After cooling to 20-25° C., MTBE was added (100 mL) and saturated aqueous $NaHCO_3$ (100 mL). The organic layer was separated and the aqueous layer washed with MTBE (1×50 mL). The combined organic phases were washed successively with saturated aqueous $NaHCO_3$ (2×50 mL). After drying over $Na_2SO_4$, the organic phase was concentrated to give 2-((4R,6S)-6-((benzo[6]thiazole-2-ylthio)methyl)-2,2-dimethyl-1,3-dioxan-4-yl) acetic acid tert-butyl ester as brown oil (D, 8.1 g, 19.7 mmol, yield 98%).

Example 4

Preparation of 2-(4R,6S)-6-((benzo[d]thiazol-2-yl-sulfonyl)methyl)-2,2-dimethyl-1,3-dioxan-4-yl)acetic acid tert-butyl ester (E) from 2-(4R,6S)-6-((benzo[d]thiazole-2-ylthio)methyl)-2,2-dimethyl-1,3-dioxan-4-yl)acetic acid tert-butyl ester (D)

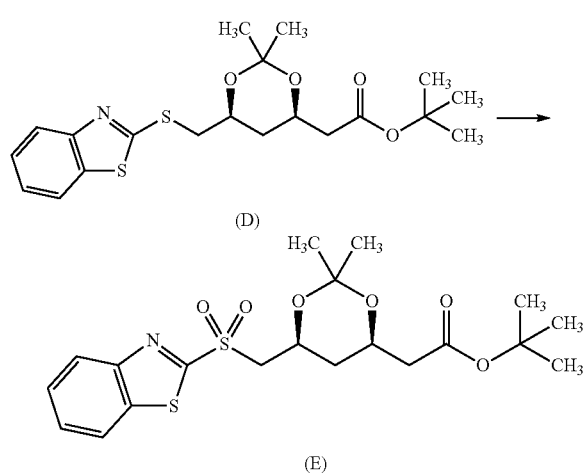

2-((4R,6S)-6-((benzo[d]thiazol-2-ylthio)methyl)-2,2-dimethyl-1,3-dioxan-4-yl)acetate tert-butyl ester (D, 8.0 g, 19.5 mmol) was dissolved in 100 mL of $CH_2Cl_2$. The solution was cooled to 0° C., followed by addition of $NaHCO_3$ (6.2 g, 73.8 mmol). Then in 2 h, MCPBA (meta-chloroperbenzoic acid, 13.7 g, 55.6 mmol, 70% purity) was added, keeping the temperature between 0 and 5° C. The thick slurry was stirred for 18 h allowing the temperature to increase to 20-25° C., followed by addition of 50 mL of $CH_2Cl_2$ and 100 mL of saturated aqueous $NaHCO_3$. The organic phase was separated and washed with saturated $NaHCO_3$ (3×50 mL). After drying over $Na_2SO_4$, the organic phase was concentrated to give 7.9 g of the crude compound of formula E. Re-crystallization from isopropanol gave 2-((4R,6S)-6 ((benzo[d]thiazole-2-yl-sulfonyl)methyl)-2,2-dimethyl-1,3-dioxan-4-yl)acetic acid tert-butyl ester as a white solid (5.2 g, 11.5 mmol, yield 59%)

Example 5

Preparation of 2-(4R,6S)-6-((benzo[d]thiazol-2-yl-sulfonyl)methyl)-2,2-dimethyl-1,3-dioxan-4-yl)acetic acid tert-butyl ester (E) from (4R,6S)-6-(chloromethyl)-2,2-dimethyl-1,3-dioxan-4-yl)acetic acid tert-butylester (A) via compound (D)

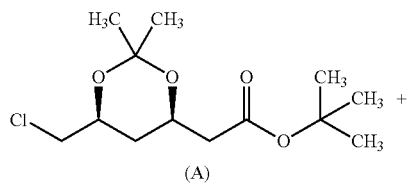

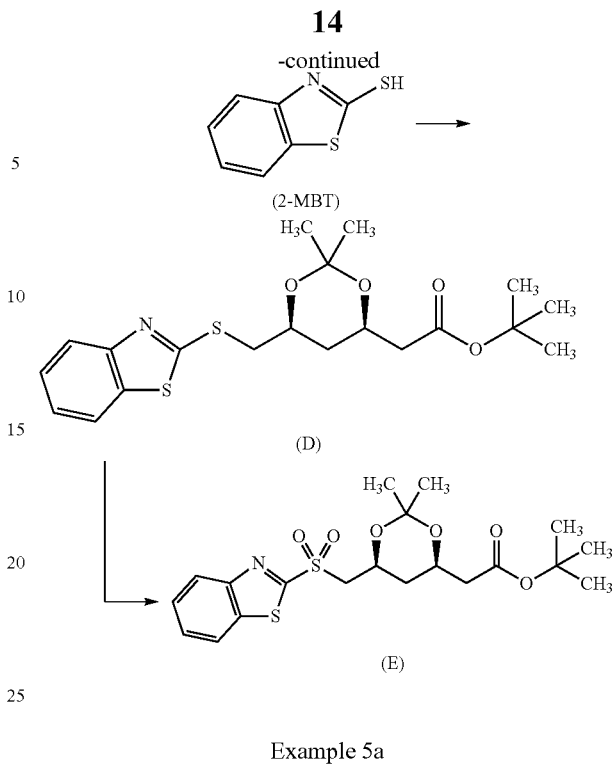

Example 5a

Potassium Carbonate as Base in Thio-Ether Synthesis

A mixture of compound A (1.39 g, 5.0 mmol), 2-mercaptobenzothiazole (2-MBT, 0.92 g, 5.5 mmol), $K_2CO_3$ (1.38 g, 10.0 mmol), and tetrabutylammonium bromide (0.16 g) in NMP (10 mL) was heated under argon at 120° C. for 4 h with stirring. Another portion of 2-MBT (0.70 g, 4.2 mmol) was added and heating was continued for 4 h. After cooling to 20-25° C., the resulting mixture was partitioned between 50 mL of MTBE and 25 mL of water and the phases were separated. The aqueous phase was extracted with 10 mL of MTBE and the unified organic phases were washed with aqueous HCl (1 N), saturated aqueous $NaHCO_3$ and brine. Evaporation of the organic solvent in vacuo left a brown oil (D, 1.72 g, 4.2 mmol, 84% yield) of which 1.66 g (4.1 mmol) was dissolved in $CH_2Cl_2$ (50 mL). $NaHCO_3$ (1.26 g, 15.0 mmol) and meta-chloroperbenzoic acid (MCPBA, 2.78 g, 11.3 mmol, 70% purity) were added. The mixture was stirred at 20-25° C. for 22 h. Saturated aqueous $NaHCO_3$ (50 mL) was added and the mixture was filtrated. The phases were separated and the organic phase was washed with saturated aqueous $NaHCO_3$, aqueous HCl (1 N) and again with saturated aqueous $NaHCO_3$. The organic phase was dried over $MgSO_4$ and evaporated to dryness in vacuo, leaving product E as highly viscous syrup that crystallized on storage at 20-25° C. (1.40 g, 78% yield). Of the product thus obtained, a sample was recrystallized from isopropanol and dried at 40° C. in vacuo to give product E as a pale yellow solid. $^1$H-NMR (400 MHz, $CDCl_3$): δ=0.75 (s, 3H); 1.24-1.33 (m, 1H) superimposed on 1.31 (s, 3H); 1.40 (s, 9H); 1.65-1.69 (m, dt-like, 1H); 2.25 (dd, J=15.3, 6.0 Hz, 1H); 2.35 (dd, J=15.3, 7.0 Hz, 1H); 3.40 (dd, J=14.7, 3.0 Hz, 1H); 3.85 (dd, J=14.7, 8.8 Hz, 1H); 4.23 ($m_c$, 1H); 4.56 ($m_c$, 1H); 7.58 ($m_c$, 2 H); 7.99 (d, 7.7 Hz, 1H); 8.19 (d, 7.7 Hz, 1H). $^{13}$C-NMR (100 MHz, $CDCl_3$): δ=19.3 ($CH_3$); 28.2 ($C(CH_3)_3$); 29.2 ($CH_3$); 35.2, 42.45 (C2, C4); 60.5 (C6); 64.6, 65.9 (C3, C5); 81.0 ($C(CH_3)_3$); 99.1 ($C(CH_3)_2$); 122.25, 125.6, 127.7, 128.1 (Ar—$C_p$); 137.0, 152.7, 166.7 (Ar—$C_q$, thiazole-$C_q$); 169.8 (C1).

Example 5b

Sodium Bicarbonate as Base in Thio-Ether Synthesis

A mixture of compound A (1.39 g, 5.0 mmol), 2-MBT (1.26 g, 7.5 mmol) and NaHCO₃ (1.26 g, 15.0 mmol), in NMP (10 mL) was heated under argon at 110° C. for 4 h with stirring. Another portion of 2-MBT (1.26 g, 7.5 mmol) was added and heating was continued for 1 h. Work-up as described in Example 3 yielded a brown oil (Compound D) of which 2.15 g was dissolved in CH₂Cl₂ (65 mL) and NaHCO₃ (2.21 g, 26.3 mmol) was added. Meta-chloroperbenzoic acid (MCPBA, 3.88 g, 15.7 mmol, 70% purity) was added portion wise in 1 h. The mixture was stirred at 20-25° C. for 16 h. Work-up as described in Example 4 yielded product E (2.23 g, yield crude 101%).

Example 6

Preparation of 2-((4R,6S)-6-((E)-2-(4-(4-fluorophenyl)-6-isopropyl-2-(N-methylmethylsulfonamido)pyrimidin-5-yl)vinyl)-2,2-dimethyl-1,3-dioxan-4-yl)acetate, tert-butyl ester (P) from N-(4-(4-fluorophenyl)-5-formyl-6-isopropylpyrimidin-2-yl)-N-methylmethanesulfonamide (J) and 2-((4R,6S)-6-((benzo[d]thiazol-2-ylsulfonyl)methyl)-2,2-dimethyl-1,3-dioxan-4-yl)acetate tert-butyl ester (E)

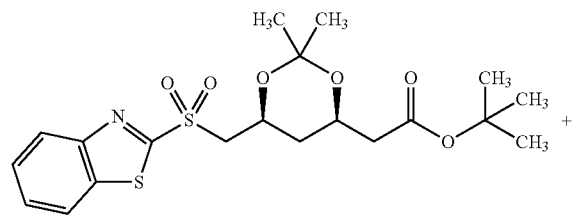

(E)

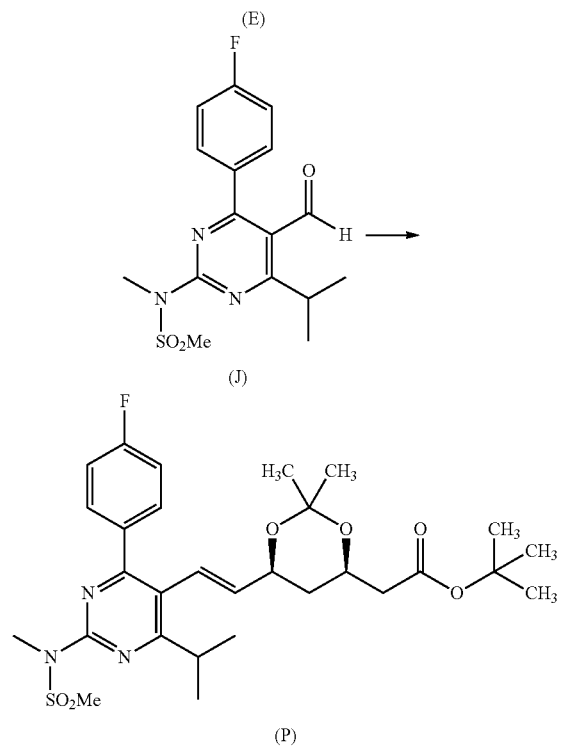

Example 6a

Using LiHMDS

N-(4-(4-fluorophenyl)-5-formyl-6-isopropylpyrimidin-2-yl)-N-methylmethanesulfonamide (J, 1.0 g, 2.9 mmol) and 2-((4R,6S)-6-((benzo[d]thiazol-2-ylsulfonyl)methyl)-2,2-dimethyl-1,3-dioxan-4-yl)acetate tert-butyl ester (E, 1.4 g, 3.1 mmol) were added to dry THF (12 mL). After stirring for 10 min at 20° C., the reaction mixture was cooled to −70° C. and 3.8 mL of LiHMDS solution (1M in THF, total 3.8 mmol) was added in 80 min keeping the temperature between −70 and −75° C. When dosing was completed, the temperature of the reaction mixture was allowed to increase to −10° C. After stirring at this temperature for 1 h, the reaction was quenched with 10% aqueous NaHCO₃ (5 mL). The phases were separated. The aqueous layer was extracted with 2×20 mL of ethyl acetate. The combined organic phases were washed with 5% aqueous Na₂CO₃ and concentrated under vacuum. HPLC analysis indicated an E to Z ratio of 70:30. The residue was crystallized from methanol to give 2-((4R,6S)-6-((E)-2-(4-(4-fluorophenyl)-6-isopropyl-2-(N-methylmethylsulfonamido) pyrimidin-5-yl)vinyl)-2,2-dimethyl-1,3-dioxan-4-yl)acetate, tert-butyl ester as a solid (P, 0.87 g, 1.5 mmol, 52% yield).

Example 6b

Using NaHMDS

N-(4-(4-fluorophenyl)-5-formyl-6-isopropylpyrimidin-2-yl)-N-methylmethanesulfonamide (0.5 g, 1.4 mmol) and 2-((4R,6S)-6-((benzo[d]thiazol-2-ylsulfonyl)methyl)-2,2-dimethyl-1,3-dioxan-4-yl)acetate tert-butyl ester (0.7 g, 1.6 mmol) were added to 10 mL of dry THF. After stirring for 10 min at 20° C., the reaction mixture was cooled to −70° C. At this temperature 1.9 mL of NaHMDS solution (1M in THF, total 3.8 mmol) was added in 60 min keeping the temperature between −70 and −75° C. When dosing was completed, the temperature of the reaction mixture was allowed to increase to −10° C. After stirring at this temperature for 1 h, the reaction was quenched with 10% aqueous NaHCO₃ (5 mL). The phases were separated. The aqueous layer was extracted with 2×20 mL of ethyl acetate. The combined organic phases were washed with 5% aqueous Na₂CO₃ and concentrated under vacuum. HPLC analysis indicated an E to Z ratio of >99:1. The residue was crystallized from methanol to give 2-((4R,6S)-6-((E)-2-(4-(4-fluorophenyl)-6-isopropyl-2-(N-methylmethylsulfonamido) pyrimidin-5-yl)vinyl)-2,2-dimethyl-1,3-dioxan-4-yl)acetate, tert-butyl ester as a solid (0.52 g, 0.9 mmol, 64% yield).

Example 7

Preparation of (4R,6S)-6-(chloromethyl)-4-(tetrahydro-2H-pyran-2-yloxy)-tetrahydro-2H-pyran-2-one (G) from (4R,6S)-6-(chloromethyl)-4-hydroxytetrahydro-2H-pyran-2-one (F)

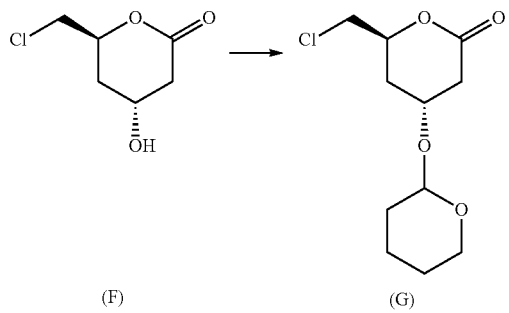 [SMILES: O=C1C[C@H](O)C[C@@H](CCl)O1 ; O=C1C[C@H](OC2CCCCO2)C[C@@H](CCl)O1 ; "(F)"]

(F)            (G)

(4R,6S)-6-(chloromethyl)-4-hydroxytetrahydro-2H-pyran-2-one (Compound F, 41.2 g, 0.25 mol) was dissolved in 250 mL of ethyl acetate at 20-25° C. Then 3,4-dihydro-2H-pyran (DHP, 29.4 g, 0.35 mol) was added. The reaction mixture was stirred for 4 h at 20-25° C. The solution was filtered and concentrated to give (4R,6S)-6-(chloromethyl)-4-(tetrahydro-2H-pyran-2-yloxy)-tetrahydro-2H-pyran-2-one (Compound G, 64.2 g, quantitative yield) as a greyish oil, which was used as such in the next step.

Example 8

Preparation of (4R,6S)-6-((benzo[6]thiazole-2-ylthio)methyl)-4-(tetrahydro-2H-pyran-2-yloxy)-tetrahydro-2H-pyran-2-one (H) from (4R,6S)-6-(chloromethyl)-4-(tetrahydro-2H-pyran-2-yloxy)-tetrahydro-2H-pyran-2-one (G) and 2-mercapto-1H-benzothiazole (2-MBT)

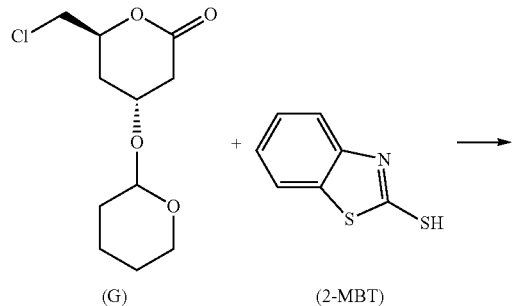

(G)                (2-MBT)

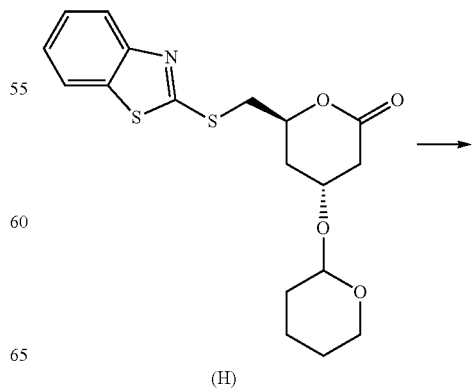

(H)

(4R,6S)-6-(chloromethyl)-4-(tetrahydro-2H-pyran-2-yloxy)-tetrahydro-2H-pyran-2-one (G, 24.7 g, 100 mmol) was dissolved in 150 mL of NMP. Then NaHCO$_3$ (12.6 g, 150 mmol) and 2-MBT (21.7 g, 130 mmol) were added, followed by 50 mL of NMP. The mixture was heated for 2 h at 70° C. and then for 7 h at 90° C. After cooling to 20-25° C., MTBE was added (300 mL) and saturated aqueous NaHCO$_3$ (300 mL). The organic layer was separated and the aqueous layer washed with MTBE (2×100 mL). The combined organic phases were washed successively with 200 mL of saturated aqueous NaHCO$_3$ and 200 mL water. After drying over Na$_2$SO$_4$, the organic phase was concentrated to give (4R,6S)-6-((benzo[6]thiazole-2-ylthio)methyl)-4-(tetrahydro-2H-pyran-2-yloxy)-tetrahydro-2H-pyran-2-one (H, 24.4 g, 64.2 mmol, yield 64.2%), as brownish oil, which was used as such in the next step.

Example 9

Preparation of (4R,6S)-6-((benzo[6]thiazole-2-ylsulfonyl)methyl)-4-(tetrahydro-2H-pyran-2-yloxy)-tetrahydro-2H-pyran-2-one (I) from (4R,6S)-6-((benzo[6]thiazole-2-ylthio)methyl)-4-(tetrahydro-2H-pyran-2-yloxy)-tetrahydro-2H-pyran-2-one (H)

-continued

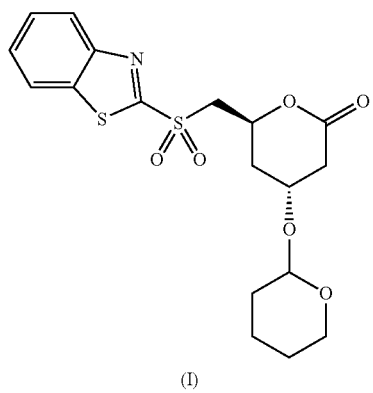

(I)

(4R,6S)-6-((benzo[6]thiazole-2-ylthio)methyl)-4-(tetrahydro-2H-pyran-2-yloxy)-tetrahydro-2H-pyran-2-one (Compound H, 23.0 g, estimated purity 70%, 42 mmol) was dissolved in 200 mL of CH₂Cl₂. The solution was cooled to 0° C., followed by addition of NaHCO₃ (14.1 g, 168 mmol). Then in 2 h, MCPBA (meta-chloroperbenzoic acid, 27.6 g, 112 mmol, 70% purity) was added, keeping the temperature between 0 and 5° C. The thick slurry was stirred for 18 h allowing the temperature to increase to 20-25° C., followed by addition of 150 mL of CH₂Cl₂ and 150 mL of saturated aqueous NaHCO₃. The organic phase was separated and washed with 3×50 mL of saturated aqueous NaHCO₃. After drying over Na₂SO₄, the organic phase was concentrated to give the crude compound of formula (1) as thick yellow oil (25.0 g, 60% pure, 36 mmol, yield 87%)

Example 10

Preparation of (4R,6S)-6-(chloromethyl)-2,2-dimethyl-1,3-dioxan-4-yl)acetic acid methyl ester (L) from (4R,6S)-6-(chloromethyl)-4-hydroxytetrahydropyran-2-one (F)

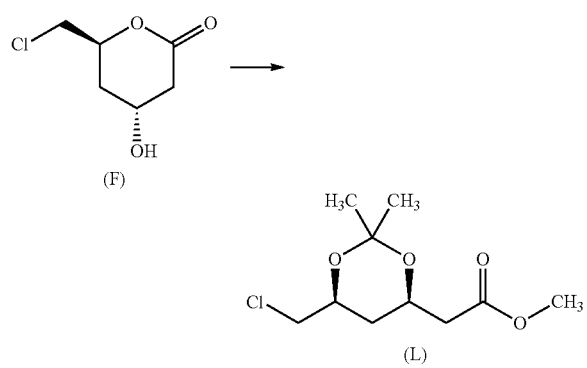

(4R,6S)-6-(chloromethyl)-4-hydroxytetrahydropyran-2-one (Compound F, 88 g, 0.53 mol) was added in 45 min to a solution of 1.0 g p-toluenesulfonic acid in 250 mL of dimethoxypropane. After stirring for 2 h at 20-22° C., 200 mL of ethyl acetate and 100 mL of saturated aqueous NaHCO₃ were added. The phases were separated and the organic phase was washed with 10% aqueous NaHCO₃ (2×100 mL). After drying over Na₂SO₄, the organic phase was concentrated to give (4R,6S)-6-(chloromethyl)-2,2-dimethyl-1,3-dioxan-4-yl)acetic acid methyl ester as a brownish oil (Compound L, 127.2 g, ~quantitative yield)

Example 11

Preparation of 2-((4R,6S)-6-((benzo[6]thiazole-2-ylthio)methyl)-2,2-dimethyl-1,3-dioxan-4-yl)acetic acid methyl ester (M) from (4R,6S)-6-(chloromethyl)-2,2-dimethyl-1,3-dioxan-4-yl)acetic acid methyl ester (L) and 2-mercapto-1H-benzothiazole (2-MBT)

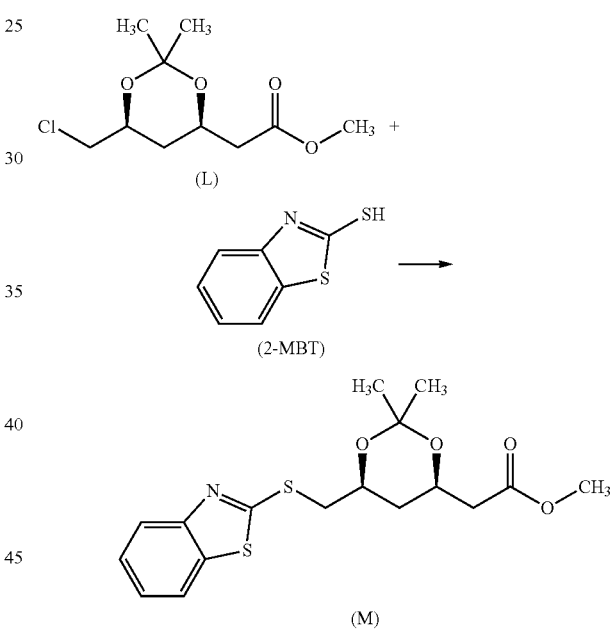

(4R,6S)-6-(chloromethyl)-2,2-dimethyl-1,3-dioxan-4-yl)acetic acid methyl ester (Compound L, 71.0 g, 0.29 mol) was dissolved in 150 mL of NMP. Then NaHCO₃ (55.4 g, 0.64 mol) and tetrabutylammonium bromide (2.0 g) were added. To the stirred mixture was added 2-mercapto-1H-benzothiazole (2-MBT, 55.1 g, 330 mmol) in about 30 min, followed by 50 mL of NMP. The mixture was heated to 110° C. and kept at this temperature for 4 h. After cooling to 20-25° C., cyclohexane was added (600 mL) and saturated aqueous NaHCO₃ (250 mL). The organic layer was separated and the aqueous layer washed with cyclohexane (2×250 mL). The combined organic phases were washed successively with 300 mL of saturated aqueous NaHCO₃ and 300 mL water. After drying over Na₂SO₄, the organic phase was concentrated to give 2-((4R,6S)-6-((benzo[6]thiazole-2-ylthio)methyl)-2,2-dimethyl-1,3-dioxan-4-yl)acetic acid methyl ester as an yellow oil (Compound M, 97.3 g, yield 89.0%).

Example 12

Preparation of 2-((4R,6S)-6-((benzo[d]thiazol-2-ylsulfonyl)methyl)-2,2-dimethyl-1,3-dioxan-4-yl)acetate methylester (N) from 2-((4R,6S)-6-((benzo[6]thiazole-2-ylthio)methyl)-2,2-dimethyl-1,3-dioxan-4-yl)acetic acid methyl ester (M)

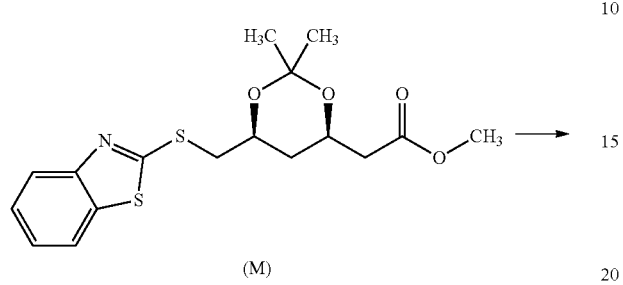

(M)

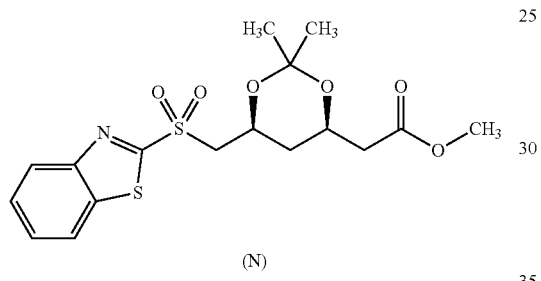

(N)

2-((4R,6S)-6-((benzo[d]thiazol-2-ylthio)methyl)-2,2-dimethyl-1,3-dioxan-4-yl)acetate methyl ester (Compound M, 95.0 g, 0.25 mol) was dissolved in 800 mL of $CH_2Cl_2$. The solution was cooled to 0° C., followed by addition of $NaHCO_3$ (79.4 g, 0.94 mol). Then in 2 h, MCPBA (meta-chloroperbenzoic acid, 172.6 g, 70% purity, 0.70 mol) was added, keeping the temperature between 0 and 5° C. Additional $CH_2Cl_2$ (250 mL) was added and the thick slurry was stirred for 18 h allowing the temperature to increase to 20-25° C. The salts were filtered, washed with 500 mL $CH_2Cl_2$ and the filtrate was concentrated to about 300 mL. Then 1 L of EtOAc was added and 300 mL of 10% aqueous $NaHSO_3$. The organic phase was separated and washed successively with 300 mL of 10% aqueous $NaHSO_3$, 2×300 mL of 5% aqueous $Na_2CO_3$ and 300 mL of water. After drying over $Na_2SO_4$, the organic phase was concentrated to give the crude compound of formula (N). The crude product was re-crystallized from 350 mL of isopropanol to give a first crop of ((4R,6S)-6-((benzo[d]thiazole-2-ylsulfonyl)methyl)-2,2-dimethyl-1,3-dioxan-4-yl)acetic acid methyl ester as a white solid (27.9 g, 0.07 mol, 28.0% yield). A second crop can be isolated from the filtrate.

Example 13

Preparation of 2-((4R,6S)-6-((E)-2-(4-(4-fluorophenyl)-6-isopropyl-2-(N-methylmethylsulfonamido)pyrimidin-5-yl)vinyl)-2,2-dimethyl-1,3-dioxan-4-yl)acetate, methyl ester (O) from N-(4-(4-fluorophenyl)-5-formyl-6-isopropylpyrimidin-2-yl)-N-methylmethanesulfonamide (J) and 2-((4R,6S)-6-((benzo[d]thiazol-2-ylsulfonyl)methyl)-2,2-dimethyl-1,3-dioxan-4-yl)acetate methyl ester (N)

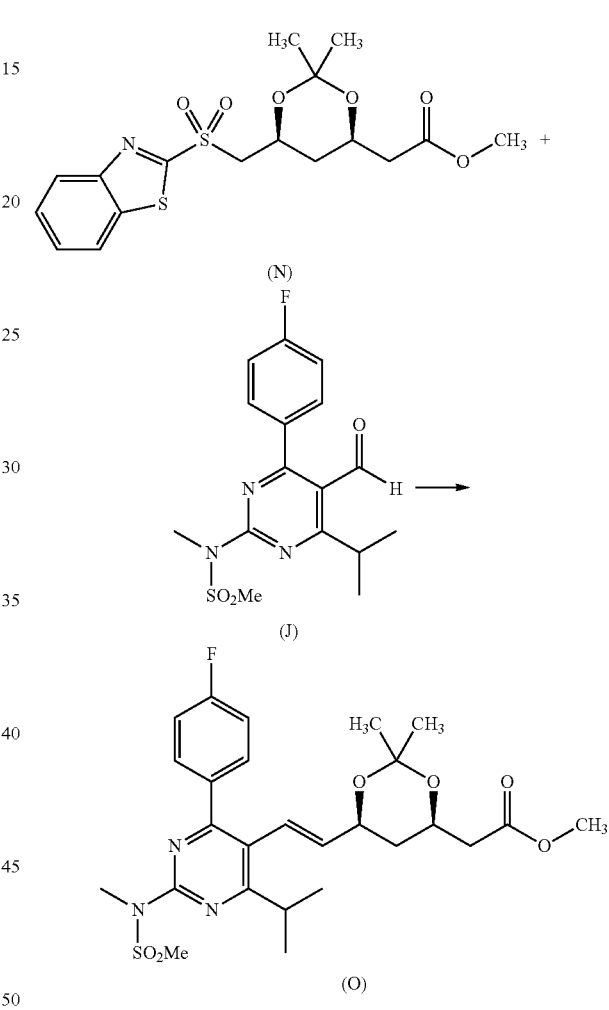

N-(4-(4-fluorophenyl)-5-formyl-6-isopropylpyrimidin-2-yl)-N-methylmethanesulfonamide (0.35 g, 1.0 mmol) and 2-((4R,6S)-6-((benzo[d]thiazol-2-ylsulfonyl)methyl)-2,2-dimethyl-1,3-dioxan-4-yl)acetate methyl ester (0.45 g, 1.1 mmol) were added to 12 mL of dry THF After stirring for 10 min at 20° C., the reaction mixture was cooled to −70° C. At this temperature 1.5 mL of NaHMDS solution (1 M in THF, total 1.5 mmol) was added in 1 h keeping the temperature between −70 and −75° C. When dosing was completed, the reaction mixture was stirred for 2 h at −75° C., then quenched with 10% aqueous $NaHCO_3$ (10 mL). The phases were separated. The aqueous layer was extracted with 2×25 mL of ethyl acetate. The combined organic phases were washed with 5% aqueous $Na_2CO_3$ and concentrated under vacuum. The residue was crystallized from isopropanol to give 2-((4R,6S)-6-((E)-2-(4-(4-fluorophenyl)-2-(N-methylmethylsulfonamido) pyrimidin-5-yl)vinyl)-2,2-dimethyl-1,3-dioxan-4-yl)acetate, methyl ester as a solid (Compound O, 0.34 g, 0.63 mmol, 63% yield).

The invention claimed is:

1. A process for the preparation of a sulfone comprising the steps of:

(a) Reacting a halomethyl substrate of general formula (1a) or (1b)

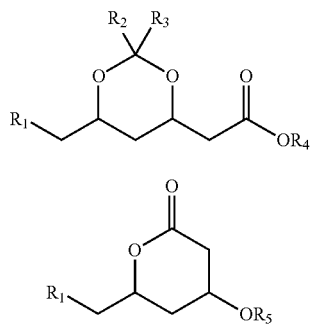

(1a)

(1b)

wherein $R_1$ is halogen, wherein $R_2$ and $R_3$ each independently stand for an alkyl with 1 to 12 carbon atoms or an alkenyl with 2 to 12 carbon atoms or a cycloalkyl with 3 to 7 carbon atoms or a cycloalkenyl with 3 to 7 carbon atoms or an aryl with 6 to 10 carbon atoms or an aralkyl with 7 to 12 carbon atoms or wherein $R_2$ and $R_3$ form a ring together with the carbon atom to which they are bound, wherein $R_4$ is an alkyl group with 1 to 4 carbon atoms or an alkenyl group with 2 to 4 carbon atoms and wherein $R_5$ is an alcohol protecting group, with a compound of general formula $R_6$—S—X wherein $R_6$ is an aryl group and X is hydrogen or an alkali metal ion or ammonium ion or tetraalkylammonium ion or phosphonium ion to obtain a compound of general formula (3a) or (3b), respectively; and

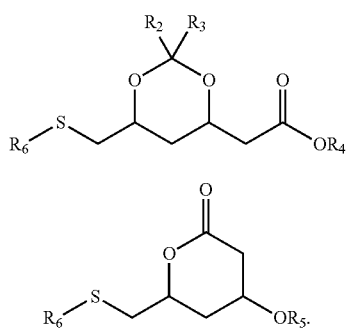

(3a)

(3b)

(b) subjecting the compound of general formula (3a) or (3b) to oxidation to thereby provide a sulfone of general formula (4a) or (4b), respectively

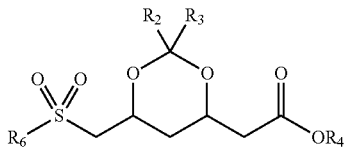

(4a)

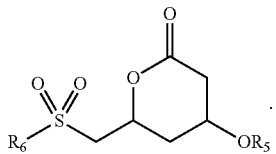

(4b)

2. The process according to claim 1, wherein $R_1$ is bromine or chlorine, $R_2$ is ethyl or methyl and $R_3$ is ethyl or methyl or $R_2$ and $R_3$ form a cyclopentyl ring or a cyclohexyl ring together with the carbon atom to which they are bound, $R_4$ is tert-butyl, ethyl, methyl, or iso-propyl, $R_5$ is methoxyethoxymethyl, tetrahydrofuranyl or tetrahydropyranyl and $R_6$ is 1-methyl-1H-tetrazol-5-yl, 1-phenyl-1H-tetrazol-5-yl, 1-tert-butyl-1-H-tetrazol-5-yl, benzothiazol-2-yl or 3,5-bis(trifluoromethyl)phenyl-1-yl.

3. The process according to claim 1, further comprising isolating the compound of general formula (3a) or (3b) and/or the compound of general formula (4a) or (4b).

4. The process according to claim 1, wherein said oxidation is carried out in the presence of hydrogen peroxide or a peracid or bleach or tert-BuOCl or a perborate or an N-oxide or a permanganate or a chromate or a chlorate or a bromate or a perchlorate or a periodate or tert-butyl hydroperoxide or oxone or a peroxodisulfate or oxygen or mixtures thereof.

5. The process according to claim 1, wherein said sulfone of general formula (4a) or (4b) is reacted with a compound of general formula $R_7$—CH=O wherein $R_7$ is 4-(4-fluorophenyl)-2,6-diisopropyl-5-(methoxymethyl)nicotinaldehyde or 3-(4-fluorophenyl)-1-isopropyl-1H-indole-2-carbaldehyde or 2-cyclopropyl-4-(4-fluorophenyl)quinoline-3-carbaldehyde or N-(4-(4-fluorophenyl)-5-formyl-6-isopropylpyrimidin-2-yl)-N-methylmethanesulfonamide to give a compound of general formula (5a) or (5b) respectively

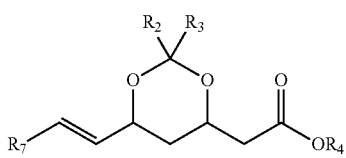

(5a)

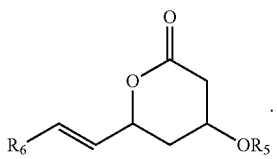

(5b)

6. The process according to claim 5, which comprises carrying out the process in the presence of a sodium-comprising base.

7. The process according to claim 6, wherein said sodium-comprising base is sodium hexamethyldisilazane.

8. The process according to claim 5, which further comprises deprotecting and isolating the compound of general formula (4a) or (4b).

9. A compound of general formula (3b) or (4b):

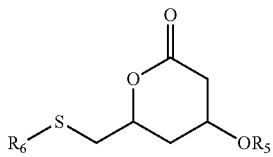
(3b)

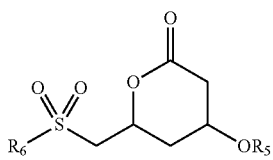
(4b)

wherein $R_5$ is hydrogen or an alcohol protecting group and $R_6$ is a radical of general formula $R_{6'}$ or $R_{6''}$

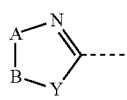
($R_{6'}$)

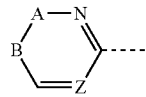
($R_{6''}$)

wherein A-B is C=C or N=N or wherein A-B is part of a aromatic five- or six-membered ring, optionally substituted, wherein Y is sulfur or an alkyl-substituted nitrogen, and wherein Z is nitrogen or CH.

10. The compound according to claim 9, wherein Y is tert-butyl-substituted nitrogen, ethyl-substituted nitrogen, methyl-substituted nitrogen or phenyl-substituted nitrogen.

11. The compound according to claim 9, wherein $R_6$ is selected from the group consisting of pyridine-2-yl, pyrimidin-2-yl, benzothiazol-2-yl, 1-methyl-1H-tetrazol-5-yl, 1-phenyl-1H-tetrazol-5-yl, 1-tert-butyl-1-H-tetrazol-5-yl, 1-methylimidazol-2-yl, benzimidazol-2-yl, 4-methyl-1,2,4-triazol-3-yl and iso-quinolin-1-yl.

* * * * *